United States Patent
Chishti et al.

(10) Patent No.: US 6,227,850 B1
(45) Date of Patent: May 8, 2001

(54) TEETH VIEWING SYSTEM

(75) Inventors: Muhammad Ziaullah Khan Chishti, Sunnyvale; Phillips Alexander Benton, Mountain View, both of CA (US)

(73) Assignee: Align Technology, Inc., Santa Clara, CA (US)

(*) Notice: Subject to any disclaimer, the term of this patent is extended or adjusted under 35 U.S.C. 154(b) by 0 days.

(21) Appl. No.: 09/313,290

(22) Filed: May 13, 1999

(51) Int. Cl.$^7$ .................................................. A61C 3/00

(52) U.S. Cl. ............................ 433/24; 433/213; 433/215

(58) Field of Search ........................... 433/24, 213, 215

(56) References Cited

U.S. PATENT DOCUMENTS

| | | | |
|---|---|---|---|
| 3,660,900 | 5/1972 | Andrews | 433/24 |
| 3,860,803 | 1/1975 | Levine | 235/151.1 |
| 4,755,139 | 7/1988 | Abbatte et al. | 433/6 |
| 4,798,534 | 1/1989 | Breads | 433/6 |
| 4,856,991 | 8/1989 | Breads et al. | 433/6 |
| 4,936,862 | 6/1990 | Walker et al. | 623/23 |
| 5,011,405 | 4/1991 | Lemchen | 433/6 |
| 5,035,613 | 7/1991 | Breads et al. | 433/6 |
| 5,055,039 | 10/1991 | Abbatte et al. | 433/24 |
| 5,059,118 | 10/1991 | Breads et al. | 433/6 |
| 5,139,419 | 8/1992 | Andreiko et al. | 433/24 |
| 5,186,623 | 2/1993 | Breads et al. | 433/6 |
| 5,273,429 | 12/1993 | Rekow | 433/215 |
| 5,338,198 | 8/1994 | Wu et al. | 433/213 |
| 5,340,309 | 8/1994 | Robertson | 433/69 |
| 5,342,202 | 8/1994 | Deshayes | 434/270 |
| 5,368,478 | 11/1994 | Andreiko et al. | 433/24 |
| 5,382,164 | 1/1995 | Stern | 433/223 |
| 5,395,238 | 3/1995 | Andreiko et al. | 433/24 |
| 5,431,562 | 7/1995 | Andreiko et al. | 433/24 |
| 5,447,432 | 9/1995 | Andreiko et al. | 433/24 |
| 5,452,219 | 9/1995 | Dehoff et al. | 364/474.05 |
| 5,454,717 | 10/1995 | Andreiko et al. | 433/24 |
| 5,474,448 | 12/1995 | Andreiko et al. | 433/24 |
| 5,528,735 | * 6/1996 | Strasnick et al. | 395/127 |
| 5,533,895 | 7/1996 | Andreiko et al. | 433/24 |
| 5,549,476 | 8/1996 | Stern | 433/223 |
| 5,587,912 | 12/1996 | Andersson et al. | 364/468.04 |
| 5,605,459 | 2/1997 | Kuroda et al. | 433/214 |
| 5,607,305 | 3/1997 | Andersson et al. | 433/223 |
| 5,645,421 | 7/1997 | Slootsky | 433/6 |

OTHER PUBLICATIONS

Biostar Operation & Training Manual, Great Lakes Orthodontics, Ltd. 199 Fire Tower Drive, Tonawanda, New York, 14150–5890, 20 pgs.

Chiappone, "cconstructingthe gnathologic setup and positioner," J. Clin. Orthod., 1980, 14:121–133.

Cottingham, "Gnathologic clear plastic positioner," Am.J.Orthod. 1969, 55:23–31.

Cureton, "Correcting malaligned mandibular incisors with removable retainers," J.Clin. Orthod. 1996. 30:390–395.

Elsasser, "Some oobservationson the history and uses of the Kesling positioner," Am. J. Orthod. 1950, 36:368–374.

Kamada et al., "Case reports on tooth positioners with LTV vinyl silicone rubber and some case reports," J. Nihon University School of Dentistry 1982, 24(1):1–27.

Kesling, "The philosophy of the tooth positioning appliance," Am. J. Orthod. Oral. Surg. 1945, 31(6):297–304.

Kesling, "Coordinating the predetermined pattern and tooth positioner with conventional treatment," Am. J. Orthod. Oral. Surg. 1946, 32:285–293.

Kleeman et al., "The speed positioner," J. Clin. Orthod. 1996, 30:673–680.

(List continued on next page.)

Primary Examiner—John J. Wilson
(74) Attorney, Agent, or Firm—Fish & Richardson P.C.

(57) ABSTRACT

A computer is used to create a plan for repositioning an orthodontic patient's teeth. The computer receives a digital data set representing the patient's teeth and uses the data sets to generate one or more orthodontic views of the patient's teeth.

38 Claims, 6 Drawing Sheets

OTHER PUBLICATIONS

Kuroda et al., "Three–dimensinal dental cast analyzing system using laser scanning," Am. J. Orthod. Dentofac. Orthop. 1996 110:365–369.

Nishiyama et al., "A new construction of tooth repositioner by LTV vinyl silicone rubber," J. Nihon Univ. School of Dentistry 1977. 19(2):93–102.

Nippon Dental Review, "New orthodontic device–dynamic positioner (D.P.)–I Approach to the proposal of D.P. and transparent silicone rubber," 1980, 452:61–74.

Nippon Dental Review, "New orthodontic device–dynamic positioner (D.P.)–II, Practice application and construction of D.P. and transparent silicone rubber," 1980, 454:107–130.

Nipon Dental Review, "New orthodontic device–dynamic positioner (D.P.)–III, Case reports of reversed occlusion," 457:146–164.

Nippon Dental Review, "New orthodontic device–dynamic positioner (D.P.)—Case reports of reversed occlusion," 1980,458:112–129.

Raintree Essix & ARS Materials, Inc., Raintree Essix, Technical Magazine Table of contents and Essix Appliances, httpz;//www.essix.com/magazine/dafault.html Aug. 13, 1997, 7 pgs.

Shilliday, "Minimizing finishing problems with the mini–positioner," Am J. Orthod. 1971, 59:596–599.

Warunek et al., "Physical and mechanical properties of elastomers in orthodonic positioners," Am. J. Orthod. Dentofac. Orthop. 1989, 95:388–400.

Wells, "Application of the positioner appliance in orthodonic treatment" Am. J. Orthodont. 1970, 58:351–366.

Lawrence F. Andrews, D.D.S., "The six to normal occlusion," Am. J. Orthod. 9/1972, 269–308.

Lawrence F. Andrews, D.D.S., "Straight Wire, The Concept and Appliance," The Six Keys to Optimal Occlusion, 15–24.

Kamada et al., "Construction of Tooth Positioners with LTV Vinyl Silicone Rubber and Some Case Reports," J. Nihon University School of Dentistry 3/1982, 24(1):1–26.

Schroeder et al., "Algoritms I," The Visualization Toolkit chapter 6–9.9, 1996.

Warunek et al., "Clinical Use of Silicone Elastomer Appliances," JCO 10/1989, 694–700.

* cited by examiner

RIGHT BUCCAL
FIG._7

LEFT BUCCAL
FIG._8

RIGHT BUCCAL OVERJET
FIG._11

LEFT BUCCAL OVERJET
FIG._10

FIG._9

ANTERIOR OVERJET

TOP

FIG._12

BOTTOM

RIGHT LINGUAL

*FIG._13*

LEFT LINGUAL

*FIG._14*

ANTERIOR

*FIG._15*

MAXILLARY OCCLUSAL

*FIG._16*

MANDIBULAR OCCLUSAL

TEETH VIEWING SYSTEM

This application is related to U.S. patent applications Ser. No. 09/169,036, entitled "System and Method for Positioning Teeth", and Ser. No. 09/169,034, entitled "Defining Tooth-Moving Appliances Computationally", both filed on Oct. 8, 1998, the full disclosures of which are incorporated herein by reference.

BACKGROUND

Field of the Invention

The invention relates generally to the field of orthodontics and, more particularly, to computer-automated development of an orthodontic treatment plan and appliance.

Orthodontics is the branch of dentistry that deals with the straightening of crooked teeth. Although there are many types of appliances that can be used by an orthodontist to straighten the teeth, the most common appliance is braces. Braces include a variety of appliances such as brackets, archwires, ligatures, and O-rings, and attaching braces to a patient's teeth is a tedious and time consuming enterprise requiring many meetings with the treating orthodontist. Consequently, conventional orthodontic treatment limits an orthodontist's patient capacity and makes orthodontic treatment quite expensive.

Before fastening braces to a patient's teeth, at least one appointment is typically scheduled with the orthodontist, dentist, and/or X-ray laboratory so that X-rays and photographs of the patient's teeth and jaw structure can be taken. Also during this preliminary meeting, or possibly at a later meeting, an alginate mold of the patient's teeth is typically made. This mold provides a model of the patient's teeth that the orthodontist uses in conjunction with the X-rays and photographs to formulate a treatment strategy. The orthodontist then typically schedules one or more appointments during which braces will be attached to the patient's teeth.

The formulation of the treatment strategy is typically a trial-and-error process where the orthodontist arrives at the treatment strategy using a mental model based on the orthodontist's experience and skill. Because an exact model is not available, the formulation of the treatment strategy is an art which is highly dependent on the estimates and judgments of the treating orthodontist. Moreover, once the treatment strategy has been generated, it is difficult to explain the expected result to the patient in words.

SUMMARY

A computer is used to create a plan for repositioning an orthodontic patient's teeth. The computer receives a digital data set representing the patient's teeth and uses the data set to generate one or more orthodontic views of the patient's teeth. The system captures three-dimensional (3D) data associated with the patient's teeth; determines a viewpoint for the patient's teeth; applies a positional transformation to the 3D data based on the viewpoint; and rendering the orthodontic view of the patient's teeth based on the positional transformation.

Implementations of the invention may include one or more of the following. The system can generate a right buccal overjet view, an anterior overject view, a left buccal overjet view, a left distal molar view, a left lingual view, a lingual incisor view, a right lingual view and a right distal molar view of the patient's teeth. A 3D graphical representation of the teeth at the positions corresponding to a selected data set can be rendered. The graphical representation of the teeth can be animated to provide a visual display of the movement of the teeth along the treatment paths. A level-of-detail compression can be applied to the selected data set to render the graphical representation of the teeth. A human user can modify the graphical representation of the teeth, which causes modifications to the selected data set in response to the instruction from the user. A graphical interface with components representing the control buttons on a video cassette recorder can be provided for a human user can manipulate to control the animation. A portion of the data in the selected data set can be used to render the graphical representation of the teeth. The human user can select a tooth in the graphical representation and read information about the tooth. The information can relate to the motion that the tooth will experience while moving along the treatment path. The graphical representation can render the teeth at a selected one of multiple viewing orthodontic-specific viewing angles. An input signal from a 3D gyroscopic input device controlled by a human user can be used to alter the orientation of the teeth in the graphical representation.

In a second aspect, a computer program, residing on a tangible storage medium for use in displaying an orthodontic view of a patient's teeth, includes executable instructions operable to cause a computer to: capture three-dimensional (3D) data associated with the patient's teeth; determine a viewpoint for the patient's teeth; apply a positional transformation to the 3D data based on the viewpoint; and render the orthodontic view of the patient's teeth based on the positional transformation.

Advantages of the invention include one or more of the following. Visualization is used to communicate treatment information in a computer-automated orthodontic treatment plan and appliance. The invention generates a realistic model of the patient's teeth without requiring a user to possess in-depth knowledge of parameters associated with a patient dental data capture system. Additionally, expertise in 3D software and knowledge of computer architecture is no longer needed to process and translate the captured medical data into a realistic computer model rendering and animation.

The invention thus allows teeth plan treatment to be generated in a simple and efficient manner. It also improves the way a treating clinician performs case presentations by allowing the clinician to express his or her treatment plans more clearly and gives a prospective patients an opportunity to visualize the facial changes associated with the proposed treatment. The invention allows multi disciplinary work teams to deal easily and efficiently with the treatment plan. Another major benefit is the ability to visualize and interact with models and processes without the attendant danger, impracticality, or significantly greater expense that would be encountered in the same environment if it were physical. Thus, money and time are saved while the quality of the treatment plan is enhanced.

DETAILED DESCRIPTION

Figure 1:
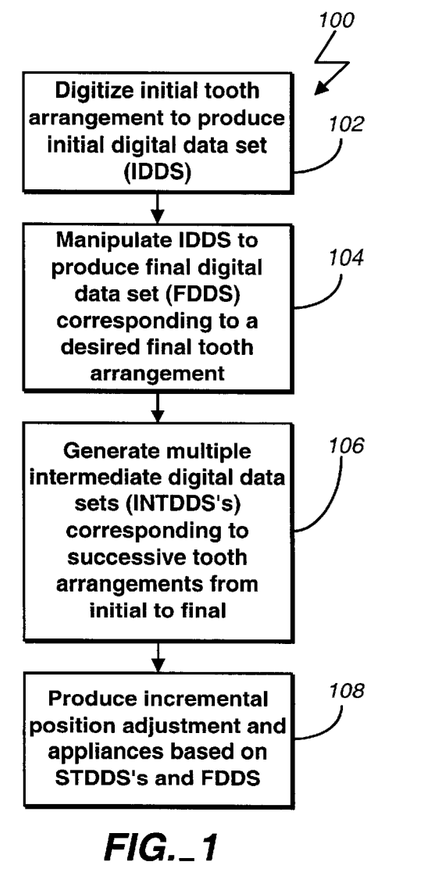
FIG. 1 is a flow chart of a process for producing a system of incremental position adjustment appliances.

FIG. 1 shows a process 100 for producing the incremental position adjustment appliances for subsequent use by a patient to reposition the patient's teeth. As a first step, an initial digital data set (IDDS) representing an initial tooth arrangement is obtained (step 102). The IDDS is then manipulated using a computer having a suitable graphical user interface (GUI) and software appropriate for viewing and modifying the images. More specific aspects of this process will be described in detail below.

Individual tooth and other components may be segmented or isolated in the model to permit their individual repositioning or removal from the digital model. After segmenting or isolating the components, the user will often reposition the tooth in the model by following a prescription or other written specification provided by the treating professional. Alternatively, the user may reposition one or more teeth based on a visual appearance or based on rules and algorithms programmed into the computer. Once the user is satisfied, the final teeth arrangement is incorporated into a final digital data set (FDDS) (step 104). The FDDS is used to generate appliances that move the teeth in a specified sequence. First, the centers of each tooth model may be aligned using a number of methods. One method is a standard arch. Then, the teeth models are rotated until their roots are in the proper vertical position. Next, the teeth models are rotated around their vertical axis into the proper orientation. The teeth models are then observed from the side, and translated vertically into their proper vertical position. Finally, the two arches are placed together, and the teeth models moved slightly to ensure that the upper and lower arches properly mesh together. The meshing of the upper and lower arches together is visualized using a collision detection process to highlight the contacting points of the teeth.

Based on both the IDDS and the FDDS, a plurality of intermediate digital data sets (INTDDSs) are defined to correspond to incrementally adjusted appliances (step 106). Finally, a set of incremental position adjustment appliances are produced based on the INTDDs and the FDDS (step 108).

In step 102, the patient's teeth may be scanned or imaged using well known technology, such as X-rays, three-dimensional X-rays, computer-aided tomographic images or data sets, and magnetic resonance images. Methods for digitizing such conventional images to produce useful data sets are well known and described in the patent and medical literature. Usually, however, a plaster cast of the patient's teeth is obtained by well known techniques, such as those described in Graber, *Orthodontics: Principle and Practice*, Second Edition, Saunders, Philadelphia, 1969, pp. 401–415.

After the tooth casting is obtained, the casting is digitally scanned by a scanner, such as a non-contact type laser or destructive scanner or a contact-type scanner, to produce the IDDS. The data set produced by the scanner may be presented in any of a variety of digital formats to ensure compatibility with the software used to manipulate images represented by the data, as described in more detail below. General techniques for producing plaster casts of teeth and generating digital models using laser scanning techniques are described, for example, in U.S. Pat. No. 5,605,459, the full disclosure of which is incorporated in this application by reference.

Suitable scanners include a variety of range acquisition systems, generally categorized by whether the acquisition process requires contact with the three dimensional object being scanned. Some contact-type scanners use probes having multiple degrees of translational and/or rotational freedom. A computer-readable (i.e., digital) representation of the sample object is generated by recording the physical displacement of the probe as it is drawn across the sample surface.

Conventional non-contact-type scanners include reflective-type and transmissive-type systems. A wide variety of reflective systems are in use today, some of which utilize non-optical incident energy sources such as microwave radar or sonar. Others utilize optical energy. Non-contact-type systems that use reflected optical energy usually include special instrumentation that carry out certain measuring techniques (e.g., imaging radar, triangulation and interferometry).

One type of non-contact scanner is an optical, reflective scanner, such as a laser scanner. Non-contact scanners such as this are inherently nondestructive (i.e., do not damage the sample object), generally are characterized by a relatively high capture resolution, and are capable of scanning a sample in a relatively short period of time. One such scanner is the Cyberware Model 15 scanner manufactured by Cyberware, Inc., Monterey, Calif.

Both non-contact-type and contact-type scanners also can include color cameras which, when synchronized with the scanning capabilities, provide means for capturing, in digital format, color representations of the sample objects. The importance of this ability to capture not just the shape of the sample object but also its color is discussed below.

Other scanners, such as the CSS-1000 model destructive scanner produced by Capture Geometry Inside (CGI), Minneapolis, Minn., can provide more detailed and precise information about a patient's teeth than a typical range acquisition scanner can provide. In particular, a destructive scanner can image areas that are hidden or shielded from a range acquisition scanner and therefore may not be subject to adequate imaging. The CSS-1000 scanner gathers image data for an object by repeatedly milling thin slices from the object and optically scanning the sequence of milled surfaces to create a sequence of 2D image slices, so none of the object's surfaces are hidden from the scanner. Image processing software combines the data from individual slices to form a data set representing the object, which later is converted into a digital representation of the surfaces of the object, as described below.

The destructive scanner may be used in conjunction with a laser scanner to create a digital model of a patient's teeth. For example, a laser scanner may be used first to build a low-resolution image of a patient's upper and lower arches coupled with the patient's wax bite, as described below. The destructive scanner then may be used to form high-resolution images of the individual arches. The data obtained by the laser scanner indicates the relation between the patient's upper and lower teeth, which later can be used to relate to each other the images generated by the destructive scanner and the digital models derived from them.

The destructive scanner can be used to form the initial digital data set (IDDS) of the patient's teeth by milling and scanning a physical model, such as a plaster casting, of the teeth. To ensure a consistent orientation of the casting throughout the destructive scanning process, a scanning system operator pots the casting in potting material, such as Encase-It epoxy from CGI, and cures the material in a pressure vacuum (PV) chamber to form a mold. Placing the potting material into the PV chamber ensures that the material sets relatively quickly with virtually no trapped air bubbles. The color of the potting material is selected to contrast sharply with the color of the casting material to ensure the clarity of the scanned image. The operator then mounts the mold to a mounting plate and places the molding plate in the destructive scanning system.

A slicing mechanism ("cutter") in the destructive scanning system mills a thin slice (typically between 0.001" and 0.006" thick) from the mold, and a positioning arm places the milled surface near an optical scanner. The optical scanner, which may be an off-the-shelf device such as a flatbed scanner or a digital camera, scans the surface to create a 2D image data set representing the surface. The positioning arm then repositions the mold below the cutter, which again mills a thin slice from mold. The resulting output of the destructive scanning system is a 3D image data set, which later is converted into a digital model of surfaces, as described in detail below. A destructive scanning system and the corresponding destructive scanning and data processing are described in U.S. Pat. No. 5,621,648.

A patient's wax bite can be used to acquire the relative positions of the upper and lower teeth in centric occlusion. For a laser scan, this can be accomplished by first placing the lower cast in front of the scanner, with the teeth facing upwards, then placing the wax bite on top of the lower cast, and finally placing the upper cast on top of the lower cast, with the teeth facing downwards, resting on the wax bite. A cylindrical scan is then acquired for the lower and upper casts in their relative positions. The scanned data provides a digital model of medium resolution representing an object which is the combination of the patient's arches positioned in the same relative configuration as in the mouth.

The digital model acts as a template guiding the placement of the two individual digital models (one per arch). More precisely, using software, for example the CyberWare alignment software, each digital arch is in turn aligned to the pair scan. The individual models are then positioned relative to each other corresponding to the arches in the patient's mouth.

The waxbite can also be scanned separately to provide a second set of data about the teeth in the upper and lower arches. In particular, the plaster cast provides a "positive" image of the patient's teeth, from which one set of data is derived, and the waxbite provides a "negative" image of the teeth, from which a second, redundant set of data is derived. The two sets of data can then be matched to form a single data set describing the patient's teeth with increased accuracy and precision. The impression from which the plaster cast was made also can be used instead of or in addition to the waxbite.

Figure 2:
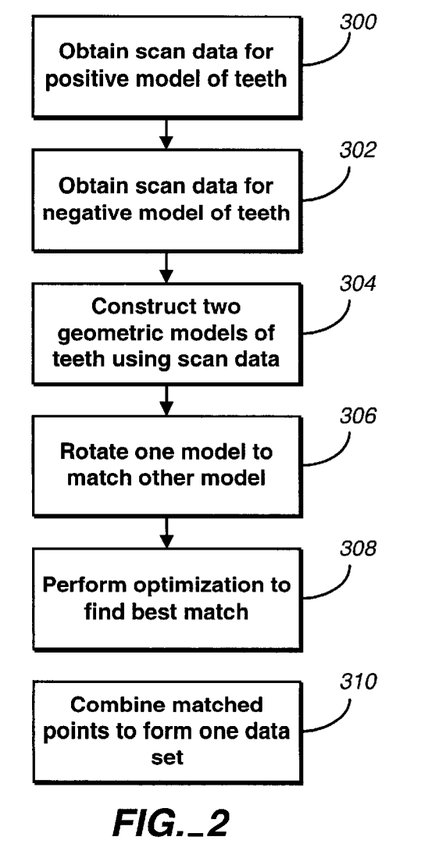
FIG. 2 is a flow chart of a process for forming one 3D image data set of teeth from two sets of image data.

FIG. 2 is a flow chart of a process for deriving a single set of data from a positive data set and a negative data set. First, scan data representing positive and negative physical tooth models is obtained (steps 300, 302). If the scan data was acquired through a destructive scanning process, two digital 3D geometric models are constructed from the data, as described below (step 304). Scan data acquired from an optical or range acquisition scanner system typically suffices as a geometric model. One of the geometric models is positioned to match roughly with the other model in the digital model space (step 306), and an optimization process is performed to determine the best match between the models (step 308). The optimization process attempts to match one point in each model to one point in the other model. Each pair of matched points then is combined into a single point to form a single set of data (step 310). The combining of matched points can be carried out in a variety of ways, for example, by averaging the coordinates of the points in each pair.

While a laser scanning system typically must perform three scans to image a patient's full set of teeth adequately (one high resolution scan for each of the upper and lower casts and a medium resolution waxbite scan), the destructive scanning system described above can image a patient's full set of teeth adequately with only a single waxbite scan. Scanning both casts with the wax bite in place ensures that all important surfaces of the upper and lower teeth are captured during a destructive scan. Scanning both casts in this manner also provides a high resolution image data set that preserves the relation between the patient's upper and lower teeth. Like the potting material described above, the wax bite should have a color that contrasts sharply with the color of the casting material to ensure the clarity of the scanned image. The wax bite may be the same color as the potting material if no contrast is desired between the waxbite and the potting material. Alternatively, the color of the wax bite may contrast sharply with the tooth casts and the potting material if an image of the wax bite is needed.

In addition to the 3D image data gathered by laser scanning or destructive scanning the exposed surfaces of the teeth, a user may wish to gather data about hidden features, such as the roots of the patient's teeth and the patient's jaw bones. This information is used to build a more complete model of the patient's dentition and to show with more accuracy and precision how the teeth will respond to treatment. For example, information about the roots allows modeling of all tooth surfaces, instead of just the crowns, which in turn allows simulation of the relationships between the crowns and the roots as they move during treatment. Information about the patient's jaws and gums also enables a more accurate model of tooth movement during treatment. For example, an x-ray of the patient's jaw bones can assist in identifying ankylose teeth, and an MRI can provide information about the density of the patient's gum tissue. Moreover, information about the relationship between the patient's teeth and other cranial features allows accurate alignment of the teeth with respect to the rest of the head at each of the treatment steps. Data about these hidden features may be gathered from many sources, including 2D and 3D x-ray systems, CT scanners, and magnetic resonance imaging (MRI) systems. Using this data to introduce visually hidden features to the tooth model is described in more detail below.

Developing an orthodontic treatment plan for a patient involves manipulating the IDDS at a computer or workstation having a suitable graphical user interface (GUI) and software appropriate for viewing and modifying the images. Specific aspects of the software will be described in detail hereinafter. However, dental appliances having incrementally differing geometries can be produced by non-computer-aided techniques. For example, plaster casts obtained as described above may be cut using knives, saws, or other cutting tools in order to permit repositioning of individual teeth within the casting. The disconnected teeth may then be held in place by soft wax or other malleable material, and a plurality of intermediate tooth arrangements can then be prepared using such a modified plaster casting of the patient's teeth. The different arrangements can be used to prepare sets of multiple appliances, generally as described below, using pressure and vacuum molding techniques.

The process of creating a 3D surface model of the teeth is discussed next. Many types of scan data, such as that acquired by an optical scanning system, provide a 3D geometric model (e.g., a triangular surface mesh) of the teeth when acquired. Other scanning techniques, such as the destructive scanning technique described above, provide data in the form of volume elements ("voxels") that can be converted into a digital geometric model of the tooth surfaces.

Figure 3:
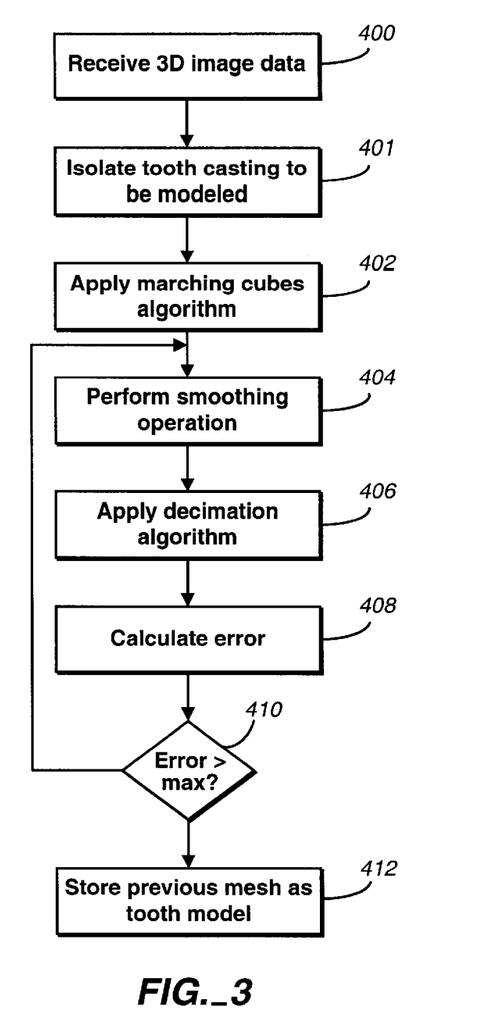
FIG. 3 is a flow chart of a process for forming a 3D surface mesh from 3D image data.

FIG. 3 is a flowchart of a process for forming a surface mesh from voxel image data. This approach involves receiving the image data from the destructive scanner (step 400), processing the data to isolate the object to be modeled (step 401), and applying a conventional "marching cubes" technique to create a surface mesh of the object (step 402).

Each set of image data can include images of multiple tooth casts or of a tooth cast and extraneous, "noisy" objects, such as air bubbles in the potting material. The system identifies each object in the image by assigning each voxel a single-bit binary value (e.g., "0" for black and "1" for white) based on the voxel's 8-bit gray scale image value, and then connecting adjacent voxels that have been assigned the same single-bit value. Each group of connected voxels represents one of the objects in the image. The system then isolates the tooth casting to be modeled by masking from the image all objects except the tooth casting of interest. The system removes noise from the masked image data by passing the data through a low-pass filter.

Once the tooth casting is isolated from the image data, the system performs a conventional marching cubes technique to locate tooth and tissue surfaces in the image data. This technique involves the identification of pairs of adjacent voxels having 8-bit image values that fall on opposite sides of a selected threshold value. Specifically, each voxel has an associated image value, typically a number between 0 and 255, that represents the image color or gray scale value at that voxel. Because the tooth casting and the surrounding potting material have sharply contrasting colors, the image values at voxels forming the image of the tooth casting differ greatly from the values at voxels forming the image of the surrounding material. Therefore, the marching cube algorithm can locate the tooth surfaces by identifying the voxels at which a sharp transition in image value occurs. The algorithm can position the surface precisely between two voxels by determining the difference between the threshold value and the image value at each voxel and then placing the surface a corresponding distance from the centerpoint of each voxel.

In some implementations, after the marching cubes algorithm is applied, the resulting mesh undergoes a smoothing operation to reduce the jaggedness on the surfaces of the tooth model caused by the marching cubes conversion (step 404). A conventional smoothing operation can be used, such as one that moves individual triangle vertices to positions representing the averages of connected neighborhood vertices to reduce the angles between triangles in the mesh.

Another optional step is the application of a decimation operation to the smoothed mesh to eliminate data points, which improves processing speed (step 406). Conventional decimation operations identify pairs of triangles that lie almost in the same plane and combine each identified pair into a single triangle by eliminating the common vertex. The decimation operation used here also incorporates orthodontic-specific decimation rules, which rely on an understanding of the general characteristics of the teeth and gums and of the orthodontic appliances that will be used to carry out a treatment plan. For example, aligners typically do not contact the portions of the tooth surfaces adjacent to the gums, so these tooth surfaces can be modeled less accurately than the rest of the tooth. The decimation operation incorporates this knowledge by decimating more heavily along the gum line. When an appliance such as a polymeric shell aligner will be used to treat the patient's teeth, the algorithm also decimates more heavily on the sides of the teeth, where the aligner usually is required only to push orthogonally to the surface, than it decimates on the tops of the teeth, where the aligner usually must form a solid grip.

After the smoothing and decimation operation are performed, an error value is calculated based on the differences between the resulting mesh and the original mesh or the original data (step 408), and the error is compared to an acceptable threshold value (step 410). The smoothing and decimation operations are applied to the mesh once again if the error does not exceed the acceptable value. The last set of mesh data that satisfies the threshold is stored as the tooth model (step 412).

Once a 3D model of the tooth surfaces has been constructed, models of the patient's individual teeth can be derived. In one approach, individual teeth and other components are "cut" to permit individual repositioning or removal of teeth in or from the digital data. After the components are "freed," a prescription or other written specification provided by the treating professional is followed to reposition the teeth. Alternatively, the teeth may be repositioned based on the visual appearance or based on rules and algorithms programmed into the computer. Once an acceptable final arrangement has been created, the final tooth arrangement is incorporated into a final digital data set (FDDS).

Based on both the IDDS and the FDDS, a plurality of intermediate digital data sets (INTDDS's) are generated to correspond to successive intermediate tooth arrangements. The system of incremental position adjustment appliances can then be fabricated based on the INTDDS's, as described in more detail below. Segmentation of individual teeth from the tooth model and determining the intermediate and final positions of teeth also are described in more detail below.

Figure 4:
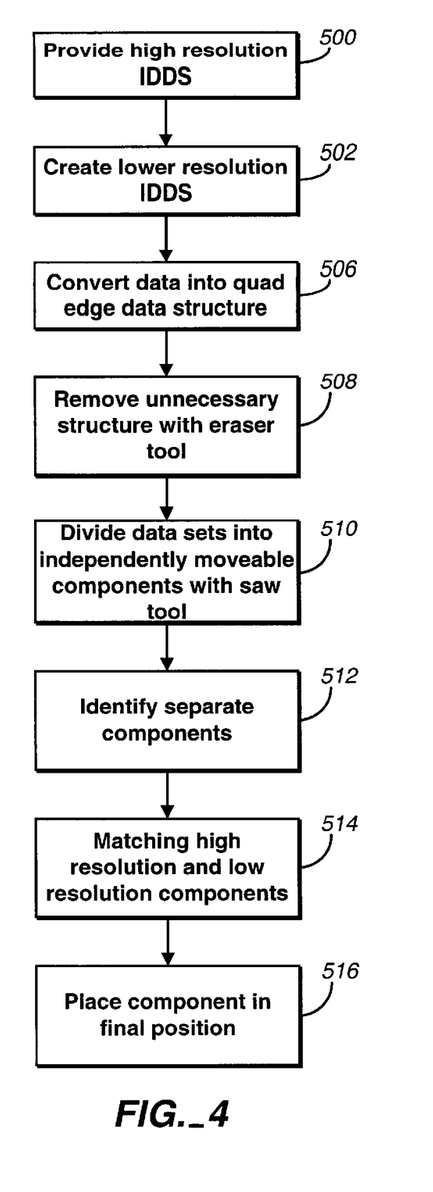
FIG. 4 is a block diagram setting forth the steps for manipulating an initial digital data set representing an initial tooth arrangement to produce a final digital data set corresponding to a desired final tooth arrangement.

FIG. 4 illustrates a representative technique for user-assisted manipulation of the IDDS to produce the FDDS on the computer. Usually, the data from the digital scanner is acquired in high resolution form (step 500). In order to reduce the computer time necessary to generate images, a parallel set of digital data representing the IDDS at a lower resolution can be created (step 502). The user can manipulate the lower resolution images while the computer updates the high resolution data set as necessary. The user can also view and manipulate the high resolution model if the extra detail provided in that model is useful. The IDDS also can be converted into a quad edge data structure if not already present in that form (step 506). A quad edge data structure is a standard topological data structure defined in *Primitives for the Manipulation of General Subdivisions and the Computation of Voronoi Diagrams*, ACM Transactions of Graphics, Vol. 4, No. 2, April 1985, pp. 74–123. Other topological data structures, such as the winged-edge data structure, could also be used.

As an initial step, while viewing the three-dimensional image of the patient's jaw, including the teeth, gingivae, and other oral tissue, the user usually deletes structure which is unnecessary for image manipulation and final production of an appliance. These unwanted sections of the model may be removed using an eraser tool to perform a solid modeling subtraction (step 508). The tool is represented by a graphic box. The volume to be erased (the dimensions, position, and orientation of the box) are set by the user employing the GUI. Typically, unwanted sections would include extraneous gum area and the base of the originally scanned cast. Another application for this tool is to stimulate the extraction of teeth and the "shaving down" of tooth surfaces. This is necessary when additional space is needed in the jaw for the final positioning of a tooth to be moved. The treating professional may choose to determine which teeth will be shaved and which teeth will be extracted. Shaving allows the patient to maintain teeth when only a small amount of space is needed. Typically, extraction and shaving are used in the treatment planning only when the actual patient teeth are to be extracted or shaved prior to initiating repositioning.

Removing unwanted or unnecessary sections of the model increases data processing speed and enhances the visual display. Unnecessary sections include those not needed for creation of the tooth repositioning appliance. The removal of these unwanted sections reduces the complexity and size of the digital data set, thus accelerating manipulations of the data set and other operations.

After the user positions and sizes the eraser tool and instructs the software to erase the unwanted section, all triangles within the box set by the user are removed and the border triangles are modified to leave a smooth, linear border. The software deletes all of the triangles within the box and clips all triangles which cross the border of the box. This requires generating new vertices on the border of the box. The holes created in the model at the faces of the box are retriangulated and closed using the newly created vertices.

In alternative embodiments, the computer automatically simplifies the digital model by performing the user-oriented functions described above. The computer applies a knowledge of orthodontic relevance to determine which portions of the digital model are unnecessary for image manipulation.

A saw tool is used to define the individual teeth (or possibly groups of teeth) to be moved (step 510). The tool separates the scanned image into individual graphic components (step 512) enabling the software to move the tooth or other component images independent of remaining portions of the model. High resolution and low resolution components are matched (step 514) and the components are placed in their final positions (step 516).

In one embodiment, the saw tool defines a path for cutting the graphic image by using two cubic B-spline curves lying in space, possibly constrained to parallel planes, either open or closed. A set of lines connects the two curves and shows the user the general cutting path. The user may edit the control points on the cubic B-splines, the thickness of the saw cut, and the number of erasers used, as described below.

In an alternative embodiment, the teeth are separated by using the saw as a "coring" device, cutting the tooth from above with vertical saw cuts. The crown of the tooth, as well as the gingivae tissue immediately below the crown are separated from the rest of the geometry, and treated as an individual unit, referred to as a tooth. When this model is moved, the gingivae tissue moves relative to the crown, creating a first order approximation of the way that the gingivae will reform within a patient's mouth.

Each tooth may also be separated from the original trimmed model. Additionally, a base may be created from the original trimmed model by cutting off the crowns of the teeth. The resulting model is used as a base for moving the teeth. This facilitates the eventual manufacture of a physical mold from the geometric model, as described below.

Thickness: When a cut is used to separate a tooth, the user will usually want the cut to be as thin as possible. However, the user may want to make a thicker cut, for example, when shaving down surrounding teeth, as described above. Graphically, the cut appears as a curve bounded by the thickness of the cut on one side of the curve.

Number of Erasers: A cut is comprised of multiple eraser boxes arranged next to each other as a piecewise linear approximation of the Saw Tool's curve path. The user chooses the number of erasers, which determines the sophistication of the curve created: the greater the number of segments, the more accurately the cutting will follow the curve. The number of erasers is shown graphically by the number of parallel lines connecting the two cubic B-spline curves. Once a saw cut has been completely specified the user applies the cut to the model. The cut is performed as a sequence of erasings.

In one embodiment, the software may automatically partition the saw tool into a set of erasers based upon a smoothness measure input by the user. The saw is adaptively subdivided until an error metric measures the deviation from the ideal representation to the approximate representation to be less than a threshold specified by the smoothness setting. One error metric compares the linear length of the subdivided curve to the arclength of the ideal spline curve. When the difference is greater than a threshold computed from the smoothness setting, a subdivision point is added along the spline curve.

A preview feature may also be provided in the software. The preview feature visually displays a saw cut as the two surfaces that represent opposed sides of the cut. This allows the user to consider the final cut before applying it to the model data set.

After the user has completed all desired cutting operations with the saw tool, multiple graphic solids exist. However, at this point, the software has not determined which triangles of the quad edge data structure belong to which components. The software chooses a random starting point in the data structure and traverses the data structure using adjacency information to find all of the triangles that are attached to each other, identifying an individual component. This process is repeated starting with the triangle whose component is not yet determined. Once the entire data structure is traversed, all components have been identified.

To the user, all changes made to the high resolution model appear to occur simultaneously in the low resolution model, and vice versa. However, there is not a one-to-one correlation between the different resolution models. Therefore, the computer "matches" the high resolution and low resolution components as best as it can subject to defined limits.

The system can optionally include a segmentation subsystem that performs automatic or semi-automatic segmentation of the 3D dentition model into models of individual teeth. The segmentation subsystem is advantageously implemented as one or more computer program processes implementing a segmentation process. In alternative implementations, the segmentation process can act on the 3D volume data or on the 3D surface mesh. The segmentation process applies conventional feature detection techniques tailored to exploit the characteristics and known features of teeth. For example, feature detection algorithms generally act on images in which the features to be distinguished from each other have different colors or shades of gray. Features to be detected also usually are separated spatially from each other. However, features to be detected in a 2D or 3D image of a plaster tooth casting (e.g., the individual teeth and the gum tissue) all have the same color (white), and some features, such as an individual tooth and the surrounding gum tissue, have no spacial separation.

The segmentation process can be implemented to employ any of several feature detection techniques and advantageously uses a combination of techniques to increase the accuracy of feature identification. One feature detection technique uses color analysis to distinguish objects based on variations in color. Color analysis can be used in situations where individual teeth are separated by gaps large enough for the potting material to fill. Because the tooth casting and the potting material have contrasting colors, these teeth appear in the model as white areas separated by thin strips of black.

Another feature detection technique uses shape analysis to distinguish certain features, such as tooth from gum. In general, tooth surfaces are smooth while gum surfaces have texture, and the teeth and gums typically form a U-shaped ridge where they meet. Detecting these features through shape analysis assists in distinguishing tooth from gum. Shape analysis can also detect individual teeth, for example by searching for the largest objects in the 3D image or by recognizing the cusps of a molar as four isolated patches of one color arranged in a certain pattern. One cusp-detection algorithm is described below.

Other feature detection techniques use databases of known cases or statistical information against which a particular 3D image is matched using conventional image pattern matching and data fitting techniques. One such technique, known as "Maximum a posteriori" (MAP), uses prior images to model pixel values corresponding to distinct object types (classes) as independent random variables with normal (Gaussian) distributions whose parameters (mean and variance) are selected empirically. For each class, a histogram profile is created based on a Gaussian distribution with the specified mean and variance. The prior images supply for each pixel and each class the probability that the pixel belongs to the class, a measure which reflects the relative frequency of each class. Applying Bayes' Rule to each class, the pixel values in the input image are scaled according to the prior probabilities, then by the distribution function. The result is a posterior probability that each pixel belongs to each class. The Maximum a posteriori (MAP) approach then selects for each pixel the class with the highest posterior probability as the output of the segmentation.

Another feature detection technique uses automatic detection of tooth cusps. Cusps are pointed projections on the chewing surface of a tooth. In one implementation, cusp detection is performed in two stages: (1) a "detection" stage, during which a set of points on the tooth are determined as candidates for cusp locations; and (2) a "rejection" stage, during which candidates from the set of points are rejected if they do not satisfy a set of criteria associated with cusps.

One process for the "detection" stage is set forth in FIG. 6A. In the detection stage, a possible cusp is viewed as an "island" on the surface of the tooth, with the candidate cusp at the highest point on the island. "Highest" is measured with respect to the coordinate system of the model, but could just as easily be measured with respect to the local coordinate system of each tooth if detection is performed after the cutting phase of treatment.

The set of all possible cusps is determined by looking for all local maxima on the tooth model that are within a specified distance of the top of the bounding box of the model. First, the highest point on the model is designated as the first candidate cusp. A plane is passed through this point, perpendicular to the direction along which the height of a point is measured. The plane is then lowered by a small predetermined distance along the Z axis. Next, all vertices connected to the tooth and which are above the plane and on some connected component are associated with the candidate cusp as cusps. This step is also referred to as the "flood fill" step. From each candidate cusp point, outward "flooding" is performed, marking each vertex on the model visited in this matter as "part of" the corresponding candidate cusp. After the flood fill step is complete, every vertex on the model is examined. Any vertex that is above the plane and has not been visited by one of the flood fills is added to the list of candidate cusps. These steps are repeated until the plane is traveled a specified distance.

While this iterative approach can be more time consuming than a local maximum search, the approach described above leads to a shorter list of candidate cusps. Since the plane is lowered a finite distance at each step, very small local maxima that can occur due to noisy data are skipped over.

After the "detection" stage, the cusp detection algorithm proceeds with the "rejection" stage. One process for the "rejection" stage is set forth in FIG. 6B. In this stage, the local geometries around each of cusp candidates are analyzed to determine if they possess "non-cusp-like features." Cusp candidates that exhibit "non-cusp-like features" are removed from the list of cusp candidates.

Various criteria may be used to identify "non-cusp-like features." According to one test, the local curvature of the surface around the cusp candidate is used to determine whether the candidate possesses non-cusp-like features. As depicted in FIG. 6B, the local curvature of the surface around the cusp candidate is approximated and then analyzed to determine if it is too large (very pointy surface) or too small (very flat surface), in which case the candidate is removed from the list of cusp candidates. Conservative values are used for the minimum and maximum curvature values to ensure that genuine cusps are not rejected by mistake.

Under an alternative test, a measure of smoothness is computed based on the average normal in an area around the candidate cusp. If the average normal deviates from the normal at the cusp by more than a specified amount, the candidate cusp is rejected. In one embodiment, the deviation of a normal vector N from the cusp normal CN is approximated by the formula:

$$\text{deviation} = 1 - \text{Abs}(N \cdot CN),$$

which is zero at no deviation, and 1 when N and CN are perpendicular.

For both the human-assisted and automated segmentation techniques, the clinician can simplify the tooth identification process by marking the physical tooth model before the model is scanned. Upon scanning, these marks become part of the digital tooth model. The types of marks that the clinician might use include marks identifying the rotational axis of a tooth, marks identifying the principal axis of a tooth (e.g., a straight line marked on the tooth's occlusal edge), and marks identifing the boundaries between teeth. A mark identifying the rotational axis of a tooth often is used to restrict how the tooth can rotate during the course of treatment. The clinician also may wish to paint the teeth in the physical model with various colors to assist in segmenting the individual teeth from the digital tooth model.

The system can optionally be configured to add roots and hidden surfaces to the tooth models to allow more thorough and accurate simulation of tooth movement during treatment. In alternative implementations, this information is added automatically without human assistance, semi-automatically with human assistance, or manually by human operator, using a variety of data sources.

In some implementations, 2D and 3D imaging systems, such as x-ray systems, computed tomography (CT) scanners, and MRI systems, are used to gather information about the roots of the patient's teeth. For example, several 2D x-ray images of a tooth taken in different planes allow the construction of a 3D model of the tooth's roots. Information about the roots is available by visual inspection of the x-ray image and by application of a computer-implemented feature identification algorithm to the x-ray data. The system adds the roots to the tooth model by creating a surface mesh representing the roots. Physical landmarks on the patient's teeth, e.g., cavities or cusps, are extracted from the 2D and 3D data and are used to register the roots to the tooth model. Like the roots, these landmarks can be extracted manually or by use of a feature detection algorithm.

Another alternative for the addition of roots and hidden surfaces is to model typical root and crown shapes and to modify the digital model of each tooth to include a root or a hidden surface corresponding to a typical shape. This approach assumes that the roots and hidden surfaces of each patient's teeth have typical shapes. A geometric model of each typical shape is acquired, e.g., by accessing an electronic database of typical root and crown models created before the analysis of a particular patient's teeth begins. Portions of the typical root and crown models are added to the individual tooth models as needed to complete the individual tooth models.

Yet another alternative for the addition of roots and hidden surfaces is the extrapolation of the 3D tooth model to include these features based on observed characteristics of the tooth surfaces. For example, the system can use the curvature of a particular molar between the tips of the cusps and the gumline to predict the shape of the roots for that molar. In other implementations, x-ray and CT scan data of a patient's teeth are used to provide comparison points for extrapolation of the patients roots and hidden surfaces. Models of typical root and crown shapes also can be used to provide comparison points for root and hidden surface extrapolation.

The system may also incorporate and the user may at any point use a "movie" feature to show an animation of the movement from initial to target states. This is helpful for visualizing overall component movement throughout the treatment process.

As described above, one suitable user interface for component identification is a three dimensional interactive graphical user interface (GUI). A three-dimensional GUI is also advantageous for component manipulation. Such an interface provides the treating professional or user with instant and visual interaction with the digital model components. The three-dimensional GUI provides advantages over interfaces that permit only simple low-level commands for directing the computer to manipulate a particular segment. In other words, a GUI adapted for manipulation is better in many ways than an interface that accepts directives, for example, only of the sort: "translate this component by 0.1 mm to the right." Such low-level commands are useful for fine-tuning, but, if they were the sole interface, the processes of component manipulation would become a tiresome and time-consuming interaction.

Before or during the manipulation process, one or more tooth components may be augmented with template models of tooth roots. Manipulation of a tooth model augmented with a root template is useful, for example, in situations where impacting of teeth below the gumline is a concern. These template models could, for example, comprise a digitized representation of the patient's teeth x-rays.

The software also allows for adding annotations to the data sets which can comprise text and/or the sequence number of the apparatus. The annotation is added as recessed text (i.e., it is 3-D geometry), so that it will appear on the printed positive model. If the annotation can be placed on a part of the mouth that will be covered by a repositioning appliance, but is unimportant for the tooth motion, the annotation may appear on the delivered repositioning appliance(s).

The above-described component identification and component manipulation software is designed to operate at a sophistication commensurate with the operator's training level. For example, the component manipulation software can assist a computer operator, lacking orthodontic training, by providing feedback regarding permissible and forbidden manipulations of the teeth. On the other hand, an orthodontist, having greater skill in intraoral physiology and teeth-moving dynamics, can simply use the component identification and manipulation software as a tool and disable or otherwise ignore the advice.

Figure 5:
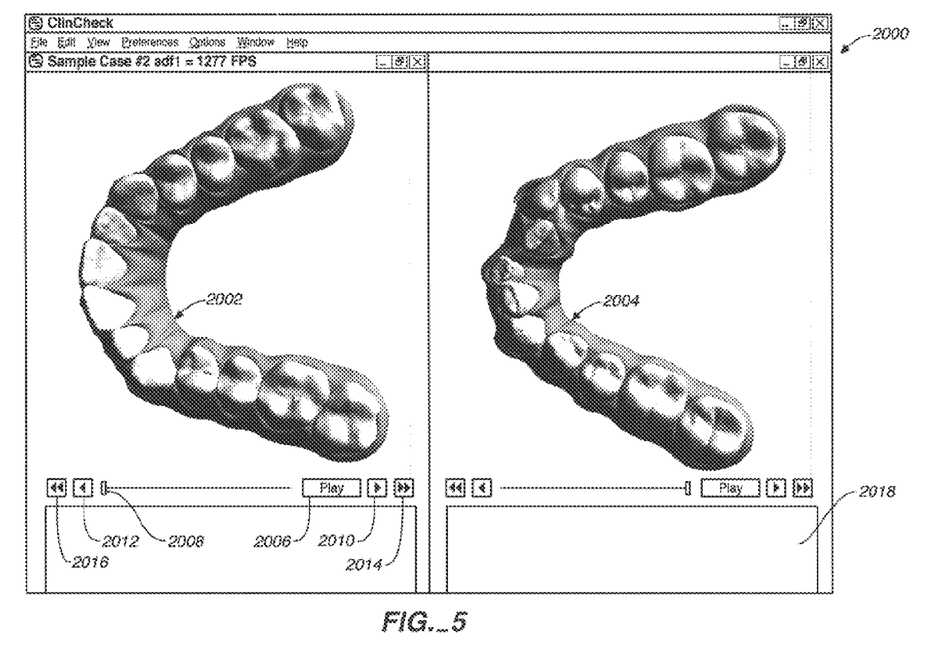
FIG. 5 is a screen shot of a GUI display used to render 3D images of an orthodontic patient's teeth.

FIG. 5 is a screen shot of the graphical user interface 2000 associated with a client viewer application through which a treating clinician is able to view a patient's treatment plan and alter or comment on the plan. The client viewer application is implemented in a computer program installed locally on a client computer at the clinician's site. The viewer program downloads a data file from a remote host, such as a file transfer protocol (FTP) server maintained by the treatment plan designer, which can be accessed either through direct connection or through a computer network, such as the World Wide Web. The viewer program uses the downloaded file to present the treatment plan graphically to the clinician. The viewer program also can be used by the treatment plan designer at the host site to view images of a patient's teeth.

Figure 6:
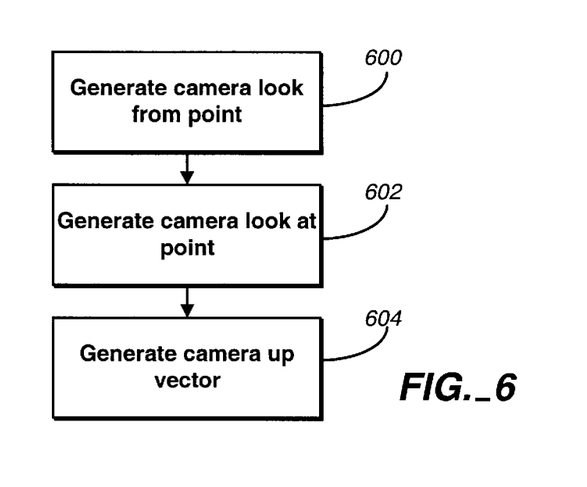
FIG. 6 is a flow chart of a process for rendering 3D images of an orthodontic patient's teeth.

FIG. 6 shows a process for rendering 3-D images of various orthodontic views that can be rendered after the patient's teeth have been digitally captured and modeled. In this process, an origin point, or "look from" point associated with a camera view is generated (step 600). Next, a "look at" point or a focus point associated with the camera view is determined (step 602). In this system, the line from LookFromPoint to LookAtPoint defines the direction the camera is shooting at. Additionally, a camera Z vector, or up vector, is determined (step 604).

Pseudo code for generating various orthodontic views is shown below. With reference to the pseudo code, the code defines a bounding box of one mold (2 arches) which is the smallest cube containing the molds geometry. Other settings associated with the bounding box include:

Z_Axis: point from lower to upper,

Y_Axis: point from inside mouse to front teeth (incisors)

X_Axis: point from center to left.

Figure 7:
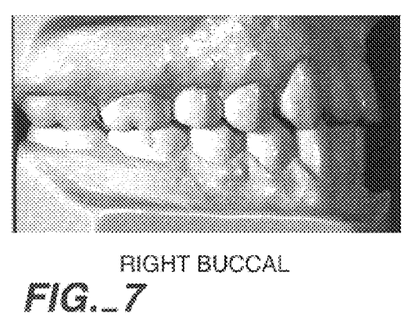
FIGS. 7–17 show exemplary 3D images of an orthodontic patient's teeth.

FieldOfView: is the open angle, it corresponding to lens
HalfFieldOfView: FieldOfView*0.5
MoldCenter: Center of the BoundingBox
X_Length: BoundingBox X dimension
Y_Length: BoundingBox X dimension
Z_Length: BoundingBox X dimension
X_MIN: minimum X value of the BoundingBox i.e. right most surface cube X value.
X_MAX: maximum X value of the BoundingBox
Y_MIN: minimum Y value of the BoundingBox
Y_MAX: maximum Y value of the BoundingBox
Z_MIN: minimum Z value of the BoundingBox
Z_MAX: maximum Z value of the BoundingBox RIGHT BUCCAL OVERJET
  CameraLookFromPoint:
    X=0.5*MoldCenter.X+0.5*X_Max+0.25*MAX(Y_Length, Z_Length)/tan(HalfFieldOfView);
    Y=MoldCenter.Y
    Z=MoldCenter.Z−0.25*MAX(Y_Length, Z_Length)/tan(HalfFieldOfView);
  CameraLookAtPoint:
    X=MoldCenter.X+0.25*X_Length;
    Y=MoldCenter.Y;
    Z=MoldCenter.Z;
  CameraUpVector: ZAxis;

ANTERIOR OVERJET
  CameraLookFromPoint:
    X=MoldCenter.X;
    Y=0.5*MoldCenter.Y+0.5*Y_Max+0.25*MAX(X_Length, Z_Length)/tan(HalfFieldOfView);
    Z=MoldCenter.Z−0.25*MAX(X_Length, Z_Length)/tan(HalfFieldOf View);
  CameraLookAtPoint:
    X=MoldCenter.X;
    Y=MoldCenter.Y+0.25*Y_Length;
    Z=MoldCenter.Z;
  CameraUpVector: ZAxis;

LEFT BUCCAL OVERJET
  CameraLookFromPoint:
    X=0.5*MoldCenter.X+0.5*X_Min−0.25*MAX(Y_Length, Z_Length)/tan(HalfFieldOfView);
    Y=MoldCenter.Y;
    Z=MoldCenter.Z−0.25*MAX(Y_Length, Z_Length)/tan(HalfFieldOfView);
  CameraLookAtPoint:
    X=MoldCenter.X−0.25*X_Length;
    Y=MoldCenter.Y;
    Z=MoldCenter.Z;
  CameraUpVector: ZAxis;

LEFT DISTAL_MOLAR
  CameraLookFromPoint:
    X=MoldCenter.X−0.25*X_Length;
    Y=Y_Min−0.25*MAX(X_Length, Z_Length)/tan(HalfFieldOfView);
    Z=MoldCenter.Z;
  CameraLookAtPoint:
    X=MoldCenter.X−0.25*X_Length;
    Y=MoldCenter.Y;
    Z=MoldCenter.Z;
  CameraUpVector: ZAxis;

LEFT LINGUAL
  CameraLookFromPoint:
    X=MoldCenter.X+0.125*X_Length;
    Y=MoldCenter.Y;
    Z=MoldCenter.Z;
  CameraLookAtPoint:
    X=MoldCenter.X−0.25*X_Length;
    Y=MoldCenter.Y;
    Z=MoldCenter.Z;
  CameraUpVector: ZAxis;

LINGUAL INCISOR
  CameraLookFromPoint:
    X=MoldCenter.X;
    Y=MoldCenter.Y;
    Z=MoldCenter.Z;
  CameraLookAtPoint:
    X=MoldCenter.X;
    Y=MoldCenter.Y+0.25*Y_Length;
    Z=MoldCenter.Z;
  CameraUpVector: ZAxis;

RIGHT LINGUAL
  CameraLookFromPoint:
    X=MoldCenter.X+0.125*X_Length;
    Y=MoldCenter.Y;
    Z=MoldCenter.Z;
  CameraLookAtPoint:
    X=MoldCenter.X+0.25*X_Length;
    Y=MoldCenter.Y;
    Z=MoldCenter.Z
  CameraUpVector: ZAxis;

RIGHT DISTAL MOLAR
  CameraLookFromPoint:
    X=MoldCenter.X+0.25*X_Length;
    Y=Y_MIN−0.25*MAX(X_Length, Z_Length)/tan(HalfieldOfView);
    Z=MoldCenter.Z;
  CameraLookAtPoint:
    X=MoldCenter.X+0.25*X_Length;
    Y=MoldCenter.Y;
    Z=MoldCenter.Z;
  CameraUpVector: ZAxis;

The eight views with which the virtual treatment models are evaluated are shown below in FIGS. 7–14. FIG. 7 shows an exemplary view of the patient's right buccal overjet. This figure shows the ideal interdigitation of the right maxillary canine, bicuspids and molars with the right mandibular canine, bicuspids and molars. FIG. 7 allows users to evaluate various aspects of the Angle classification.

Figure 8:
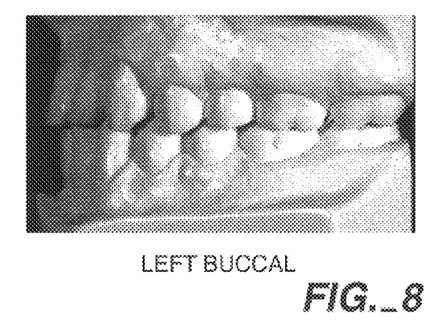
Figure 9:
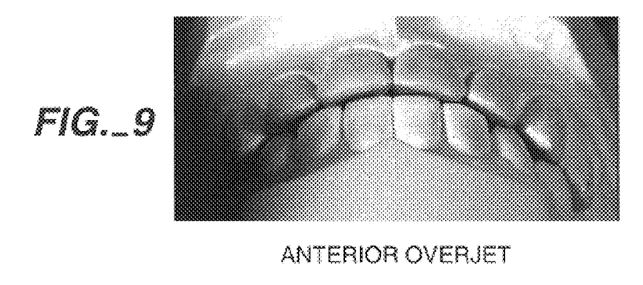
Figure 10:
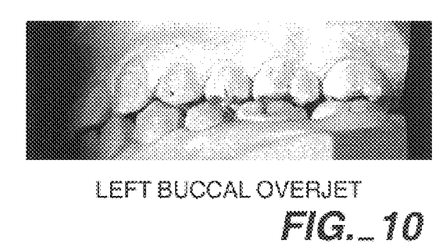
Figure 11:
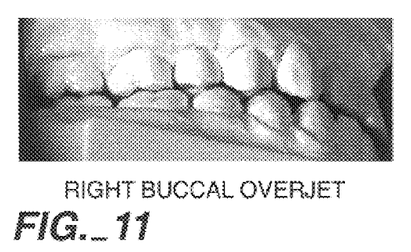
Figure 12:
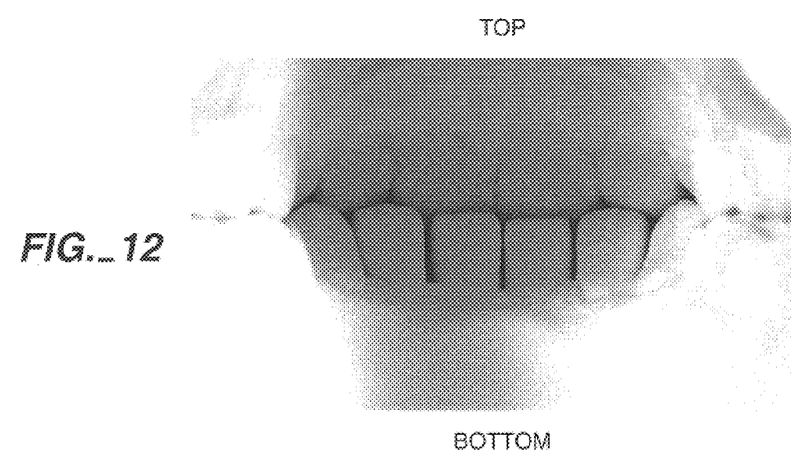

FIG. 8 shows an example view of the patient's left buccal overjet. The view shows the ideal interdigitation of the left maxillary canine, bicuspids and molars with the left mandibular canine, bicuspids and molars. FIG. 8 also allows an evaluation of Angle classification. FIG. 9 shows an exemplary view of the patient's anterior overjet and shows how far forward are the maxillary incisors in relation to the mandibular incisors. FIG. 9 allows the user to evaluate the midline. FIG. 10 shows an exemplary view of the patient's right distal molar. This figure shows the cusp and fossa relationship between the maxillary and mandibular molars. FIG. 11 shows an exemplary left distal molar view of the patient's teeth. The view of FIG. 11 shows the cusp and fossa relationship between the maxillary and mandibular molars. FIG. 12 shows an exemplary lingual incisor view of the patient's teeth. The view illustrates how the incisal edge of the mandibular incisors relate with lingual aspect of the maxillary incisors an allows a midline evaluation.

Figure 13:
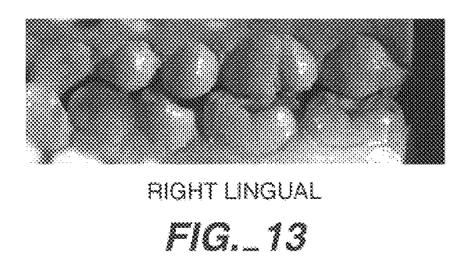

FIG. 13 shows a right lingual view and provides a close view of the inter-cuspation of the posterior right segment from the lingual aspect. FIG. 13 allows a visualization of ML(mesio-ligual) cusps of maxillary molars and their relationship with the fossae of mandibular molars.

Figure 14:
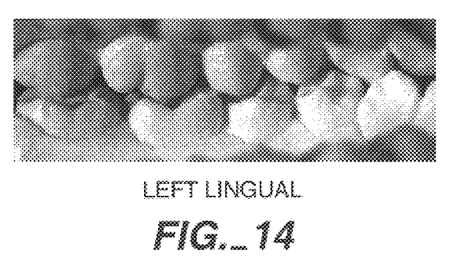

FIG. 14 shows the left lingual view of the patient's teeth. It shows a close view of the inter-cuspation of the posterior left segment from the lingual aspect and allows a visualization of ML(mesio-ligual) cusps of maxillary molars and their relationship with the fossae of mandibular molars.

Figure 15:
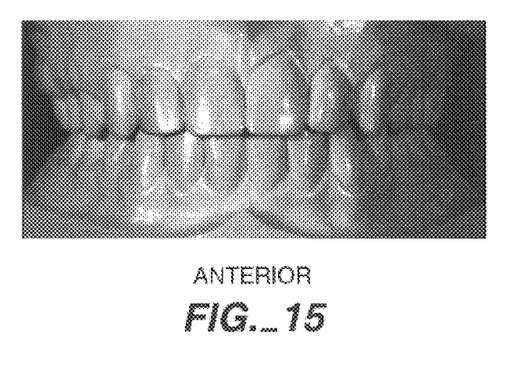
Figure 16:
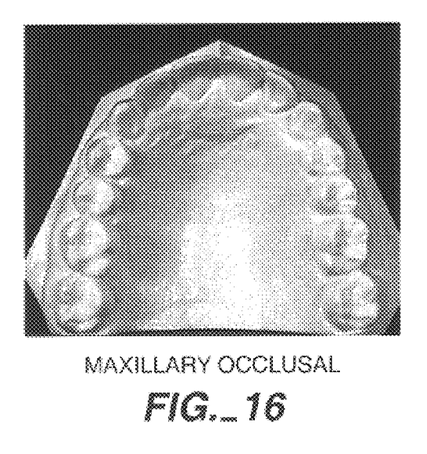
Figure 17:
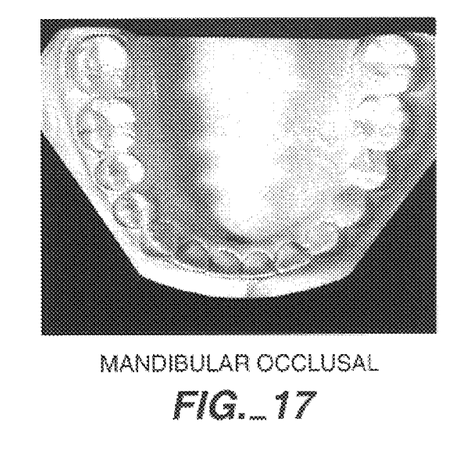

In addition to the above views, other views may be generated. For instance, FIG. 15 shows an anterior view, FIG. 16 shows a maxillary occlusal view, and FIG. 17 shows a mandibular occlusal view, respectively.

The data downloaded by the viewer program contains a fixed set of key treatment positions, including the IDDS and the FDDS, that define the treatment plan for the patient's teeth. The viewer program renders the IDDS or the FDDS to display an image of the patient's teeth at the initial and final positions. The viewer program can display an image of the teeth at their initial positions (initial image 2002) and the final tooth positions (final image 2004) concurrently.

Because the data file contains a large amount of data, the download software in the remote host employs a "level-of-detail" technique to organize the download into data groups with progressively increasing levels of detail, as described below. The viewer program uses knowledge of orthodontic relevance to render less important areas of the image at a lower quality than it renders the more important areas. Use of these techniques reduces the time required to generate a single rendered image of the tooth models and the time required to display a rendered image on the screen after the download has begun.

Figure 18:
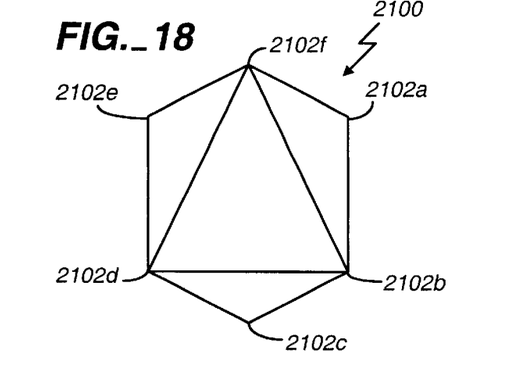
FIGS. 18–19 illustrate a technique for improving the downloading and rendering speed of an orthodontic image data file.

FIGS. 18 and 19 illustrate the use of the "level-of-detail" technique by the download software in the remote host. The software transfers the data in several groups, each of which adds detail incrementally for the rendered image of the teeth. The first group typically includes just enough data to render a rough polygon representation of the patient's teeth. For example, if a tooth is treated as a cube having six faces, the tooth can be rendered quickly as a diamond 2100 having six points 2102a–f, one lying in each face of the cube (FIG. 18). The download software begins the download by delivering a few points for each tooth, which the interface program uses to render polygon representations of the teeth immediately.

Figure 19:
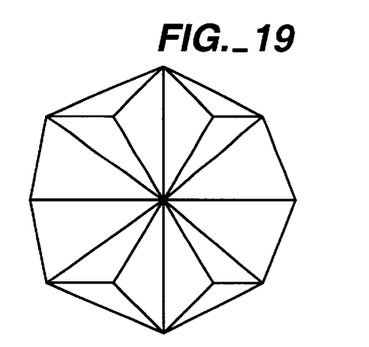

The download software then delivers a second data group that adds additional detail to the rendered images of the teeth. This group typically adds points that allow a spheroid representation 2106 of the teeth (FIG. 19). As the download continues, the software delivers additional groups of data, each adding a level of detail to the rendered image of the teeth, until the teeth are fully rendered.

The download software also improves download and rendering speed by identifying and withholding data that is not critical to forming a rendered image of the teeth. This includes data for tooth surfaces obscured by other teeth or by tissue. The software applies rules based on common orthodontic structure to determine which data is downloaded and which is withheld. Withholding data in this manner reduces the size of the downloaded file and therefore reduces the number of data points that the interface program must take into account when rendering the initial and final images.

The viewer program also improves rendering speed by reducing the amount of data rendered. Like the download software, the viewer program applies rules of orthodontic relevance to determine which areas of the image can be rendered at lower quality. For example, the treating clinician usually does not want to view gum tissue in detail, so the viewer program renders the gums at low resolution as smooth surfaces, ignoring data that preserves the texture of the gums. Typically, the viewer program renders the less important areas at lower resolution before rendering the more important areas at higher resolution. The clinician can request high resolution rendering of the entire image.

As shown in FIGS. 5–6 and discussed above, the viewer program displays an initial image 2002 of the teeth and, if requested by the clinician, a final image 2004 of the teeth as they will appear after treatment. The clinician can rotate the images in three dimensions to view the various tooth surfaces, and the clinician can snap the image to any of several predefined viewing angles. As discussed in more detail above in conjunction with FIGS. 7–17, these viewing angles include the standard front, back, top, bottom and side views, as well as orthodontic-specific viewing angles, such as the lingual, buccal, facial, occlusal, and incisal views.

The viewer program also includes an animation routine that provides a series of images showing the positions of the teeth at each intermediate step along the treatment path. The clinician controls the animation routine through a VCR metaphor, which provides control buttons similar to those on a conventional video cassette recorder. In particular, the VCR metaphor includes a "play" button 2006 that, when selected, causes the animation routine to step through all of the images along the treatment path. A slide bar 2008 moves horizontally a predetermined distance with each successive image displayed. Each position of the slide bar 2008 and each image in the series corresponds to one of the intermediate treatment steps described above.

The VCR metaphor also includes a "step forward" button 2010 and a "step back" button 2012, which allow the clinician to step forward or backward through the series of images, one key frame or treatment step at a time, as well as a "fast forward" button 2014 and a "fast back" button 2016, which allow the clinician to jump immediately to the final image 2004 or initial image 2002, respectively. The clinician also can step immediately to any image in the series by positioning the slide bar 2008 at the appropriate location.

As described above, the viewer program receives a fixed subset of key positions, including the IDDS and the FDDS, from the remote host. From this data, the animation routine derives the transformation curves required to display the teeth at the intermediate treatment steps, using any of a variety of mathematical techniques. One technique is by invoking the path-generation program described above. In this situation, the viewer program includes the path-generation program code. The animation routine invokes this code either when the downloaded key positions are first received or when the user invokes the animation routine.

The viewer program allows the clinician to alter the rendered image by manipulating the image graphically. For example, the clinician can reposition an individual tooth by using a mouse to click and drag or rotate the tooth to a desired position. In some implementations, repositioning an individual tooth alters only the rendered image; in other implementations, repositioning a tooth in this manner modifies the underlying data set. In the latter situation, the viewer program performs collision detection to determine whether the attempted alteration is valid and, if not, notifies the clinician immediately. Alternatively, the viewer program modifies the underlying data set and then uploads the altered data set to the remote host, which performs the collision detection algorithm. The clinician also can provide textual feedback to the remote host through a dialog box 2018 in the interface display 2000. Text entered into the dialog box 2018 is stored as a text object and later uploaded to the remote host or, alternatively, is delivered to the remote host immediately via an existing connection.

The viewer program optionally allows the clinician to isolate the image of a particular tooth and view the tooth apart from the other teeth. The clinician also can change the color of an individual tooth or group of teeth in a single rendered image or across the series of images. These features give the clinician a better understanding of the behavior of individual teeth during the course of treatment.

Another feature of the viewer program allows the clinician to receive information about a specific tooth or a specific part of the model upon command, e.g., by selecting the area of interest with a mouse. The types of information available include tooth type, distance between adjacent teeth, and forces (magnitudes and directions) exerted on the teeth by the aligner or by other teeth. Finite element analysis techniques are used to calculate the forces exerted on the teeth. The clinician also can request graphical displays of certain information, such as a plot of the forces exerted on a tooth throughout the course of treatment or a chart showing the movements that a tooth will make between steps on the treatment path. The viewer program also optionally includes "virtual calipers," a graphical tool that allows the clinician to select two points on the rendered image and receive a display indicating the distance between the points.

Figure 20:
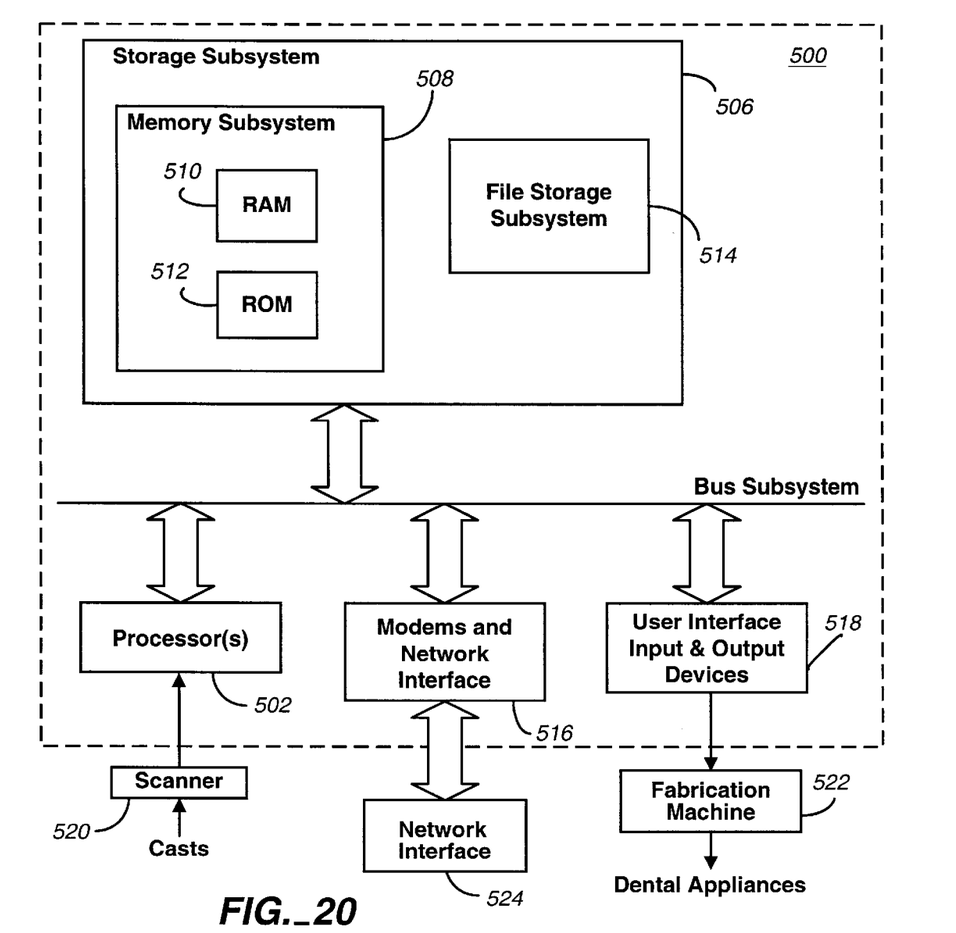
FIG. 20 is a simplified block diagram of a data processing system.

FIG. 20 is a simplified block diagram of a data processing system 300 that may be used to develop orthodontic treatment plans. The data processing system 300 typically includes at least one processor 302 which communicates with a number of peripheral devices via bus subsystem 304. These peripheral devices typically include a storage subsystem 306 (memory subsystem 308 and file storage subsystem 314), a set of user interface input and output devices 318, and an interface to outside networks 316, including the public switched telephone network. This interface is shown schematically as "Modems and Network Interface" block 316, and is coupled to corresponding interface devices in other data processing systems via communication network interface 324. Data processing system 300 could be a terminal or a low-end personal computer or a high-end personal computer, workstation or mainframe.

The user interface input devices typically include a keyboard and may fuirther include a pointing device and a scanner. The pointing device may be an indirect pointing device such as a mouse, trackball, touchpad, or graphics tablet, or a direct pointing device such as a touchscreen incorporated into the display, or a three dimensional pointing device, such as the gyroscopic pointing device described in U.S. Pat. No. 5,440,326, other types of user interface input devices, such as voice recognition systems, can also be used.

User interface output devices typically include a printer and a display subsystem, which includes a display controller and a display device coupled to the controller. The display device may be a cathode ray tube (CRT), a flat-panel device such as a liquid crystal display (LCD), or a projection device. The display subsystem may also provide non-visual display such as audio output.

Storage subsystem 306 maintains the basic required programming and data constructs. The program modules discussed above are typically stored in storage subsystem 306. Storage subsystem 306 typically comprises memory subsystem 308 and file storage subsystem 314.

Memory subsystem 308 typically includes a number of memories including a main random access memory (RAM) 310 for storage of instructions and data during program execution and a read only memory (ROM) 312 in which fixed instructions are stored. In the case of Macintosh-compatible personal computers the ROM would include portions of the operating system; in the case of IBM-compatible personal computers, this would include the BIOS (basic input/output system).

File storage subsystem 314 provides persistent (non-volatile) storage for program and data files, and typically includes at least one hard disk drive and at least one floppy disk drive (with associated removable media). There may also be other devices such as a CD-ROM drive and optical drives (all with their associated removable media). Additionally, the system may include drives of the type with removable media cartridges. The removable media cartridges may, for example be hard disk cartridges, such as those marketed by Syquest and others, and flexible disk cartridges, such as those marketed by Iomega. One or more of the drives may be located at a remote location, such as in a server on a local area network or at a site on the Internet's World Wide Web.

In this context, the term "bus subsystem" is used generically so as to include any mechanism for letting the various components and subsystems communicate with each other as intended. With the exception of the input devices and the display, the other components need not be at the same physical location. Thus, for example, portions of the file storage system could be connected via various local-area or wide-area network media, including telephone lines. Similarly, the input devices and display need not be at the same location as the processor, although it is anticipated that personal computers and workstations typically will be used.

Bus subsystem 304 is shown schematically as a single bus, but a typical system has a number of buses such as a local bus and one or more expansion buses (e.g., ADB, SCSI, ISA, EISA, MCA, NuBus, or PCI), as well as serial and parallel ports. Network connections are usually established through a device such as a network adapter on one of these expansion buses or a modem on a serial port. The client computer may be a desktop system or a portable system.

Scanner 320 is responsible for scanning casts of the patient's teeth obtained either from the patient or from an orthodontist and providing the scanned digital data set information to data processing system 300 for fuirther processing. In a distributed environment, scanner 320 may be located at a remote location and communicate scanned digital data set information to data processing system 300 via network interface 324.

Fabrication machine 322 fabricates dental appliances based on intermediate and final data set information received from data processing system 300. In a distributed environment, fabrication machine 322 may be located at a remote location and receive data set information from data processing system 300 via network interface 324.

The invention has been described in terms of particular embodiments. Other embodiments are within the scope of the following claims. For example, the three-dimensional scanning techniques described above may be used to analyze material characteristics, such as shrinkage and expansion, of the materials that form the tooth castings and the aligners. Also, the 3D tooth models and the graphical interface described above may be used to assist clinicians that treat patients with conventional braces or other conventional orthodontic appliances, in which case the constraints applied to tooth movement would be modified accordingly. Moreover, the tooth models may be posted on a hypertext transfer protocol (http) web site for limited access by the corresponding patients and treating clinicians.

What is claimed is:

1. A method for displaying an orthodontic view of a patient's teeth, comprising:

capturing three-dimensional (3D) data associated with the patient's teeth;

determining a viewpoint for the patient's teeth;

applying a positional transformation to the 3D data based on the viewpoint;

rendering a graphical representation of the patient's teeth based on the positional transformation;

determining a treatment path for each tooth; and updating the graphical representation of the teeth to provide a visual display of the position of the teeth along the treatment paths.

2. The method of claim 1, further comprising generating a right buccal ovejet view of the patient's teeth.

3. The method of claim 1, further comprising generating an anterior ovedject view of the patient's teeth.

4. The method of claim 1, further comprising generating a left buccal overjet view of the patient's teeth.

5. The method of claim 1, further comprising generating a left distal molar view of the patient's teeth.

6. The method of claim 1, further comprising generating a left lingual view of the patient's teeth.

7. The method of claim 1, further comprising generating a lingual incisor view of the patient's teeth.

8. The method of claim 1, further comprising generating a right lingual view of the patient's teeth.

9. The method of claim 1, further comprising generating a right distal molar view of the patient's teeth.

10. The method of claim 1, further comprising rendering a 3D graphical representation of the teeth at the positions corresponding to a selected data set.

11. The method of claim 1, further comprising applying a level-of-detail compression to the selected data set to render the graphical representation of the teeth.

12. The method of claim 1, further comprising receiving an instruction from a human user to modify the graphical representation of the teeth.

13. The method of claim 12, further comprising modifying the selected data set in response to the instruction from the user.

14. The method of claim 1, further comprising providing a graphical interface, with components representing the control buttons on a video cassette recorder, which a human user can manipulate to control the animation.

15. The method of claim 1, further comprising using only a portion of the data in the selected data set to render the graphical representation of the teeth.

16. The method of claim 1, further comprising allowing a human user to select a tooth in the graphical representation and, in response, displaying information about the tooth.

17. The method of claim 16, wherein the information relates to the motion that the tooth will experience while moving along the treatment path.

18. The method of claim 1, wherein rendering the graphical representation comprises rendering the teeth at a selected one of multiple viewing orthodontic-specific viewing angles.

19. The method of claim 1, further comprising receiving an input signal from a 3D gyroscopic input device controlled by a human user and using the input signal to alter the orientation of the teeth in the graphical representation.

20. A computer program, residing on a tangible storage medium, for use in displaying an orthodontic view of a patient's teeth, the program comprising executable instructions operable to cause a computer to:

capture three-dimensional (3D) data associated with the patient's teeth;

determine a viewpoint for the patient's teeth;

apply a positional transformation to the 3D data based on the viewpoint; and render a graphical representation of the patient's teeth based on the positional transformation;

determine a treatment path for each tooth; and update the graphical representation of the teeth to provide a visual display of the position of the teeth along the treatment paths.

21. The computer program of claim 20, further comprising instruction to generate a right buccal overjet view of the patient's teeth.

22. The computer program of claim 20, further comprising instructions to generate an anterior overject view of the patient's teeth.

23. The computer program of claim 20. further comprising instructions to generate a left buccal overjet view of the patient's teeth.

24. The computer program of claim 20, further comprising instructions to generate a left distal molar view of the patient's teeth.

25. The computer program of claim 20, fuirther comprising generating a left lingual view of the patient's teeth.

26. The computer program of claim 20, further comprising generating a lingual incisor view of the patient's teeth.

27. The computer program of claim 20, further comprising instructions to generate a right lingual view of the patient's teeth.

28. The computer program of claim 20, further comprising instructions to generate a right distal molar view of the patient's teeth.

29. The computer program of claim 20, further comprising instructions to render a 3D graphical representation of the teeth at the positions corresponding to a selected data set.

30. The computer program of claim 20, further comprising instructions to apply a level-of-detail compression to the selected data set to render the graphical representation of the teeth.

31. The computer program of claim 20, further comprising instructions to receive an instruction from a human user to modify the graphical representation of the teeth.

32. The computer program of claim 31, further comprising instructions to modify the selected data set in response to the instruction from the user.

33. The computer program of claim 20, further comprising instructions to provide a graphical interface, with components representing the control buttons on a video cassette recorder, which a human user can manipulate to control the animation.

34. The computer program of claim 20, further comprising instructions to use only a portion of the data in the selected data set to render the graphical representation of the teeth.

35. The computer program of claim 20, further comprising instructions to allow a human user to select a tooth in the graphical representation and, in response, displaying information about the tooth.

36. The computer program of claim 35, wherein the information relates to the motion that the tooth will experience while moving along the treatment path.

37. The computer program of claim 20, wherein the instructions to render the graphical representation comprises instructions to render the teeth at a selected one of multiple viewing orthodontic-specific viewing angles.

38. The computer program of claim 20, further comprising instructions to receive an input signal from a 3D gyroscopic input device controlled by a human user and using the input signal to alter the orientation of the teeth in the graphical representation.

\* \* \* \* \*